United States Patent [19]

Cotting et al.

[11] Patent Number: 5,322,907

[45] Date of Patent: Jun. 21, 1994

[54] HARDENERS FOR POWDER COATING COMPOSITIONS BASED ON POLYESTER RESINS

[75] Inventors: Jacques-Alain Cotting, Bonnefontaine, Switzerland; Philippe Gottis, Mulhouse, France

[73] Assignee: Ciba-Geigy Corporation, Ardsley, N.Y.

[21] Appl. No.: 856,240

[22] Filed: Mar. 25, 1992

[30] Foreign Application Priority Data

Mar. 27, 1991 [CH] Switzerland ............................ 939/91

[51] Int. Cl.$^5$ .............................................. C08F 20/20
[52] U.S. Cl. .................................. 525/438; 528/220; 528/271; 528/370; 528/403; 525/437; 525/449; 525/471; 525/523; 525/533
[58] Field of Search ............... 525/437, 438, 449, 471, 525/523, 533; 528/220, 271, 370, 403

[56] References Cited

U.S. PATENT DOCUMENTS

| | | | |
|---|---|---|---|
| 3,344,117 | 9/1967 | Bamford et al. | 528/112 |
| 3,397,254 | 8/1968 | Wynstra et al. | 525/438 |
| 3,941,725 | 3/1976 | Schmitter et al. | 521/135 |
| 4,102,701 | 7/1978 | Campbell et al. | 106/111 |
| 4,112,012 | 9/1978 | de Cleur et al. | 525/438 |
| 4,145,370 | 3/1979 | Sreeves | 525/438 |
| 4,147,737 | 4/1979 | Sein et al. | 525/438 |
| 4,340,698 | 7/1982 | De Jongh et al. | 525/438 |
| 4,681,811 | 7/1987 | Simpson et al. | 428/413 |
| 4,703,101 | 10/1987 | Singer et al. | 528/87 |

FOREIGN PATENT DOCUMENTS

| | | |
|---|---|---|
| 0365428 | 4/1990 | European Pat. Off. . |
| 0366608 | 5/1990 | European Pat. Off. . |
| 0383601 | 8/1990 | European Pat. Off. . |
| 1409835 | 10/1975 | United Kingdom . |

OTHER PUBLICATIONS

Henry Lee Kris Neville, "Handbook of Epoxy Resins" MacGraw-Hill, Inc. 1967 p. 2-2.
Ullmann's Encyclopedia of Industrial Chemistry, Fifth Edition, vol. A9, p. 559.

Handbook of Epoxy Resins, MacGraw-Hill Inc. 1967, Appendix 5-1.
Derwent Abst. 90-134038/18.

Primary Examiner—Samuel A. Acquah
Attorney, Agent, or Firm—William A. Teoli, Jr.

[57] ABSTRACT

The invention relates to the use of polyglycidyl compounds as hardeners in powder coating compositions based on polyester resins which react with epoxy groups, which compounds are polyglycidyl esters of formula (I) or (II)

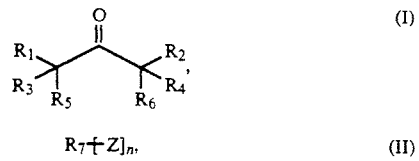

$R_7 + Z]_n,$  (II)

wherein in formula (I)
$R_1$, $R_2$, $R_3$ and $R_4$ are each independently of one another hydrogen, $C_1$-$C_4$alkyl or radicals of formula (III)

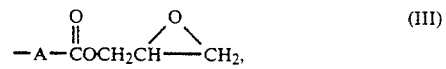

wherein A is a polymethylene group of 2 to 4 carbon atoms, and
$R_5$ and $R_6$ are each independently of each other hydrogen, $C_1$-$C_4$alkyl or radicals of formula (III) or, when taken together, are an unsubstituted or a $C_1$-$C_4$alkyl-substituted methylene or polymethylene group of 2 to 7 carbon atoms, but with the proviso that at least two of the substituents $R_1$ to $R_6$ are radicals of formula (III), and, in formula (II)
n is an integer from 2 to 6,
$R_7$ is an organic radical of valency n of 2 to 30 carbon atoms, and
Z denotes identical or different radicals of formula (IV):

(Abstract continued on next page.)

ABSTRACT
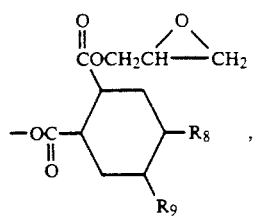
wherein $R_8$ and $R_9$ are either each independently of the other hydrogen, chloro, bromo or $C_1$-$C_4$alkyl or one is a radical of formula (V)
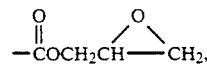
and the other is hydrogen, chloro, bromo or $C_1$-$C_4$alkyl, and the six-membered ring in formula (IV) is aromatic or non-aromatic.
5 Claims, No Drawings

HARDENERS FOR POWDER COATING COMPOSITIONS BASED ON POLYESTER RESINS

The present invention relates to the use of specific polyglycidyl compounds as hardeners based on polyester resins which react with epoxy groups, to powder coating compositions containing these components, and to a special use of said powder coating compositions.

Polyglycidyl compounds have been widely proposed as crosslinking agents or hardeners for powder coating compositions based on polyester resins. Triglycidyl isocyanurate in particular has gained acceptance in practice as hardener for outdoor coatings which must have superior durability (q.v. Ullmann's Encyclopedia of Industrial Chemistry, 5th Ed., Vol A9, p. 559). Although triglycidyl isocyanurate has proven for this utility, when used as hardener for polyester resins with which superior outdoor weathering properties are obtained, the resultant coatings often have only rather poor flexibility and are therefore more susceptible to mechanical stress. If, conversely, polyester resins which form more flexible films are used together with triglycidyl isocyanurate as hardener, the weatherability of the coatings could frequently be even better. At the present time therefore, one is obliged to give preference to one of the cited properties and, depending on the importance of said properties, to choose a suitable polyester resin.

In EP-A-0 383 601 the use of triglycidyl trimellitate is proposed as hardener for polyester resin powder coating compositions. However, triglycidyl trimellitate also has the same shortcomings as those of triglycidyl isocyanurate referred to above.

The present invention has for its object to provide compounds useful as hardeners for polyester resin powder coating compositions which make it possible to produce coatings which simultaneously meet the requirements of weatherability and flexibility to a high degree. In particular, the hardeners shall have this advantage when also used in conjunction with polyesters which have been developed for powder coating compositions which are curable with triglycidyl isocyanurate.

This object is achieved by using polyglycidyl compounds as hardeners in polyester resin powder coating compositions which react with epoxy groups, which compounds are polyglycidyl esters of formula (I) or (II)

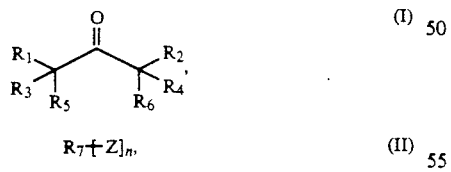  (I)

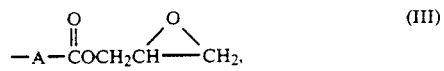  (II)

wherein in formula (I)

$R_1$, $R_2$, $R_3$ and $R_4$ are each independently of one another hydrogen, $C_1$–$C_4$alkyl or radicals of formula (III):

$$-A-\overset{O}{\overset{\|}{C}}OCH_2CH\overset{O}{\diagup\diagdown}CH_2. \quad (III)$$

wherein A is a polymethylene group of 2 to 4 carbon atoms, and $R_5$ and $R_6$ are each independently of each other hydrogen, $C_1$–$C_4$alkyl or radicals of formula (III) or, when taken together, are an unsubstituted or a $C_1$–$C_4$alkyl-substituted methylene or polymethylene group of 2 to 7 carbon atoms, but with the proviso that at least two of the substituents $R_1$ to $R_6$ are radicals of formula (III), and, in formula (II)

n is an integer from 2 to 6, $R_7$ is an organic radical of valency n containing 2 to 30 carbon atoms, and Z denotes identical or different radicals of formula (IV)

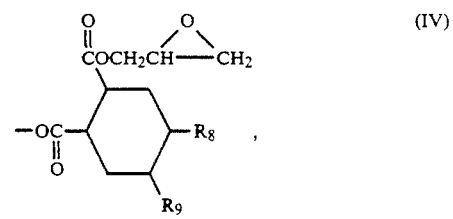  (IV)

wherein $R_8$ and $R_9$ are either each independently of the other hydrogen, chloro, bromo or $C_1$–$C_4$alkyl or one is a radical of formula (V):

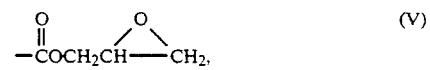  (V)

and the other is hydrogen, chloro, bromo or $C_1$–$C_4$alkyl, and the six-membered ring in formula (IV) is aromatic or non-aromatic.

The invention further relates to powder coating compositions comprising at least one polyglycidyl compound and a polyester resin which reacts therewith, which compound is a polyglycidyl ester of formula (I) or (II) as defined above.

Some of the polyglycidyl compounds of formula (I) or (II) are novel compounds.

Compounds of formula (I) are especially preferred if in formula (III) A is an ethylene group.

Representative examples of particularly useful compounds of formula (I) are the 2,2,5,5-tetra(β-carboxyethyl)cyclopentanone tetraglycidyl ester, the 2,2,6,6-tetra(β-carboxyethyl)cyclohexanone tetraglycidyl ester and the 2,2,4,4-tetra(β-carboxyethyl)pentan-3-one tetraglycidylester or 1,1,3,3-tetra(β-carboxyethyl)acetone tetraglycidyl ester.

$R_1$ to $R_4$ in formula (I) further each denote preferably a radical of formula (III) and $R_5$ and $R_6$ are preferably together an unsubstituted or a $C_1$–$C_4$alkyl-substituted methylene or polymethylene group of 2 to 7 carbon atoms, more particularly an unsubstituted polymethylene group of 2 to 4 carbon atoms. The number of alkyl substituents may be up to twice the number of carbon atoms of the methylene or polymethylene group, but should desirably be only 1 or 2.

The compounds are obtainable from the corresponding polycarboxylic acids, conveniently by reacting the carboxylic acids with epihalohydrin to give the halohydrin esters, halogen being preferably chloro or bromo. The halohydrin esters can thereafter be dehydrohalogenated with hydrogen halide acceptors to give the corresponding glycidyl esters as described in detail in DE-A-23 19 815 (=GB 1 409 835). The starting cycloaliphatic polycarboxylic acids can be prepared in general accordance with GB patent 1 033 697 (=U.S. Pat. No. 4,102,701).

In formula (II) $R_7$ is preferably a divalent to hexavalent, more particularly a divalent, trivalent or tetravalent, aliphatic radical of 2 to 10 carbon atoms, a corresponding cycloaliphatic or aromatic radical containing 5 to 10 ring carbon atoms or an araliphatic radical containing 5 to 20 ring carbon atoms in which also one or more of the aromatic nuclei can be hydrogenated up to partial or complete saturation. These radicals may also contain hetero atoms. The radicals $R_7$ can be considers as the residues of polyalcohols or polyols from which the hydroxyl groups have been removed in an amount corresponding to the number n or, preferably, to one of the valences given above. Particularly preferred radicals $R_7$ are those derived from straight chain and branched chain aliphatic polyols, typically from glycols such as ethylene or propylene glycol, from glycerol, trimethylolpropane, erythritol or pentaerythritol. Another example is sorbitol. Preferred polyols are also bisphenol types, typically 2,2-bis(4-hydroxyphenyl)propane or bis(4-hydroxyphenyl)methane, and similar wholly or partially saturated compounds, for example 2,2-bis(4-hydroxycyclohexyl)propane. In some cases the polyols can also be dimerised or prepolymerised, i.e. they can be polyether alcohols such as polyethylene glycols or bis(trimethylol)propane. The prepolymers preferably have a degree of polymerisation of 2 to 6.

The six-membered carbon ring in formula (IV) can be either aromatic or cycloaliphatic, in which latter case it may be wholly or only partially saturated. It may carry further substituents, typically chloro, bromo or $C_1$-$C_4$alkyl. Dependant on the degree of saturation of the ring, the ring may carry up to 10 substituents; but for practical reasons it will expediently carry not more than 4 substituents. Most preferably, however, the ring will contain only the glycidyl ester groups as substituents.

The individual substituents Z in formula (II) may also be different. They also need not have the identical number of glycidyl ester groups.

The compounds of formula (II) are especially suitable for the invention, in particular when $R_7$ is a divalent to tetravalent radical which is derived from an aliphatic polyalcohol or polyether polyol of 2 to 10 carbon atoms by removal of two to four hydroxyl groups, or when $R_7$ is a divalent to tetravalent, preferably divalent, radical of the molecular formula

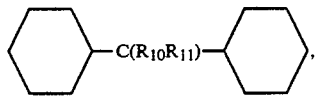

in which $R_{10}$ and $R_{11}$ are each independently of the other hydrogen or methyl and the six-membered carbon rings may be aromatic or non-aromatic.

Also preferred are the compounds of formula (II) which contain altogether at least 4 glycidyl ester groups.

The compounds of formula (II) can be obtained in the following manner. First the chosen polyalcohol is reacted to the hemiester with phthalic, tetrahydrophthalic, hexahydrophthalic or trimellitic anhydride, which may be hydrogenated up to partial or total saturation, or with a derivative of said anhydrides which carries the substituents cited above in respect of $R_8$ and/or $R_9$, in the appropriate stoichiometric ratio. In the case of trimelletic anhydride, which carries a carboxyl group in addition to the anhydride group, virtually only the anhydride group reacts to a hemiester carrying two carboxyl groups. The carboxyl groups can subsequently be glycidylised with epihalohydrin, preferably epichlorohydrin, as described above in respect of the compounds of formula (I).

The compounds of formula (I) and (II) are typically hardeners for powder coating compositions based on polyester resins which contain functional groups that react with epoxy groups, typically hydroxyl, thiol, amino, amido or carboxyl groups. Further examples of suitable functional groups will be found in Henry Lee, Kris Neville, "Handbook of Epoxy Resins", MacGraw-Hill, Inc. 1967, Appendix 5-1. The use of a catalyst can be expedient in the case of many functional groups.

Polyesters carrying terminal carboxyl groups are preferred. Preferably the polyesters have an acid number (given in mg of KOH/g of polyester) of 10 to 100 and a molecular weight of 500 to 10 000, preferably of up to 2000. The polyesters are preferably solid at room temperature and have a glass transition temperature of 35° to 120° C., preferably of 40° to 80° C.

The polyesters described in the foregoing paragraph are disclosed in U.S. Pat. No. 3,397,254. They are reaction products of polyols with dicarboxylic acids and, in some cases, polyfunctional carboxylic acids or carboxylic acid anhydrides. Representative examples of suitable polyols are ethylene glycol, propylene glycol, 1,3-butanediol, 1,4-butanediol, neopentanediol, isopentyl glycol, 1,6-hexanediol, glycerol, trimethylolethane, trimethylolpropane, erythritol, pentaerythritol or cyclohexanediol. In particular neopentanediol constitutes an essential constituent of the polyester resins which are suitable for very durable coatings. Typical examples of suitable dicarboxylic acids are isophthalic acid, terephthalic acid, phthalic acid, methylphthalic acids, tetrahydrophthalic acid, methyltetrahydrophthalic acids. For example 4-methyltetrahydrophthalic acid, cyclohexanedicarboxylic acid, succinic acid, glutaric acid, adipic acid, pimelic acid, suberic acid, azelaic acid, sebacic acid, fumaric acid, maleic acid, or 4,4'-diphenyldicarboxylic acid and the like. Suitable tricarboxylic anhydrides are the anhydrides of aliphatic tricarboxylic acid, such as 1,2,3-propanetricarboxylic acid, of aromatic tricarboxylic acid, such as trimellitic acid (benzene-1,2,4-tricarboxylic acid) and hemimellitic acid (benzene-1,2,3-tricarboxylic acid), or of cycloaliphatic tricarboxylic acid, such as 6-methylcyclohex-4-ene-1,2,3-tricarboxylic acid. Exemplary of suitable tetracarboxylic anhydrides are pyromellitic dianhydride or benzophenone-3,3',4,4'-tetracarboxylic dianhydride.

The glycidyl compounds of formulae (I) and (II) are preferably used in an amount such that the ratio of carboxyl groups to epoxy groups in the powder coating composition is from 0.5:1 to 2:1. They may be used by themselves or in admixture with other glycidyl esters of formulae (I) or (II). In some cases it may also be advantageous to add other types of epoxy hardeners customarily used for powder coating compositions.

The powder coating compositions can contain still other modifiers conventionally used in the coating industry, typically light stabilisers, dyes, pigments such as titanium dioxide pigment, dearating agents such as benzoin, and/or flow control agents. Suitable flow control agents are typically polyvinyl acetals such as polyvinyl butyral, polyethylene glycol, polyvinyl pyrrolidone, glycerol, and the acrylic copolymers available under the registered trademarks Modaflow ® [MONSANTO] or Acrylron ® [PROTEX].

A special embodiment of the novel powder coating compositions comprises a polyester which carries terminal carboxyl groups, and a polyglycidyl ester of formula (II), in which $R_7$ is a divalent to tetravalent radical which is derived from an aliphatic polyalcohol or polyether polyol of 2 to 10 carbon atoms by removal of two to four hydroxyl groups, or $R_7$ is a divalent to tetravalent, preferably divalent, radical of the following molecular formula

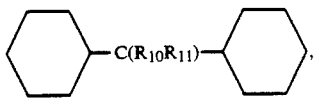

wherein $R_{10}$ and $R_{11}$ are each independently of the other hydrogen or methyl and the six-membered carbon rings may be aromatic or non-aromatic.

The powder coating compositions of this invention can be prepared by simple mixing of the components, conveniently in a ball mill. Another possibility comprises fusing, mixing and homogenising the components together, preferably in an extruder, as in a Buss Ko-kneader, cooling the product and comminuting it. Especially if the glycidyl ester components are flowable, it can be useful to prepare first a masterbatch from the glycidyl components and to prepare at least a part of the polyester material, as the material can be well stored in this form and, for use, can be readily processed with the other desired components to the final powder coating composition. The powder coating compositions preferably have a particle size in the range from 0.015 to 500 μm, most preferably from 10 to 75 μm.

After application to the coated object, the powder coating compositions are cured at a temperature of not less than c. 100° C., preferably 150° to 250° C. Normally about 5 to 60 minutes are required for the cure. Suitable for coating are all materials which are stable at the temperatures necessary for the cure, preferably ceramic materials and metals.

It is especially preferred to use the above described crosslinking agents for polyesters which have a very high content of aromatic dicarboxylic acids, such as phthalic acid and terephthalic acid, in conjunction with neopentanediol as alcoholic component, typically containing up to at least 80 percent by weight, preferably up to 90 percent by weight and more, of neopentanediol and aromatic dicarboxylic acids as components. Inventive powder coating compositions which contain such polyesters that are commercially available under the registered trademarks Crylcoat ® types [UCB], Uralac ® [DSM] or Grilesta ® [EMS], have on the one hand very superior outdoor durability and, on the other, are usually very flexible both under sudden as well as permanent mechanical stress. It follows from what has been said above that the novel powder coating compositions are especially suitable for outdoor coatings owing to their weather-resistance. The invention therefore also relates to the use of the novel powder coating compositions for producing weather-resistant coatings.

EXAMPLE 1

Glycidylation of 2,2,6,6-tetra(β-carboxyethyl)cyclohexanone

To 500 g (1.3 mol) of 2,2,6,6-tetra(β-carboxyethyl)cyclohexanone (preparation described in EP-A-0 366 608) are added 3413 g (36.9 mol) of epichlorohydrin and the temperature is kept at 100° C. Then 31 g of a 50% aqueous solution of tetramethylammonium chloride are added. The temperature is kept between 96° and 100° C. and the reaction course is monitored using a pH electrode. After c. 90 minutes, the pH meter registers a sudden increase to a value of c. 10, thereby indicating the end of the addition reaction. After removal of the pH electrode, the reaction mixture is cooled to 50° C. and another 31 g of the 50% aqueous solution of tetramethylammonium chloride are added. Under a vacuum of 0.09 to 0.13 bar and at a temperature of 48°–53° C., 463.7 g of a 50% aqueous solution of sodium hydroxide are run in continuously while distilling the resulting water from the reaction mixture with epichlorohydrin as an azeotropic mixture. The epichlorohydrin is separated from the water in a water separator and returned to the reaction mixture continuously. A total of c. 360 g of water can be separated. Afterwards the reaction mixture is washed with 200 ml of a 10% aqueous solution of monosodium phosphate and with 3×300 ml of water. The washed reaction mixture is concentrated on a rotary evaporator under a water jet vacuum. The residue is dried for 20 minutes at 130° C./0.0013 bar, giving 675.6 g (85% of theory) 2,2,6,6-tetra(β-carboxyethyl)cyclohexanone tetraglycidyl ester in the form of a yellow viscous oil (epoxy value 5.90 equivalents, corresponding to 90% of theory, chlorine content 1.43%).

EXAMPLE 2

Preparation of a masterbatch from 2,2,6,6-tetra(β-carboxyethyl)cyclohexanone tetraglycidyl ester and a polyester A mixture of 800 g of Crylcoat ® 430 (carboxyl-terminated polyester based on neopentanediol and terephthalic acid, with an acid value of c. 30 mg of KOH/g and a glass transition temperature ($T_G$) of c. 70° C. (DSC), manufactured by UCB, Belgium) and 160 g of 2,2,6,6-tetra(β-carboxyethyl)cyclohexanone tetraglycidyl ester is homogenised in an extruder (Ko-kneader supplied by Buss, Pratteln, CH) at a temperature in the range from 30° to 110° C., preferably from 70° to 90° C. The cooled extrudate is comminuted to a particle size of c. 2.4 mm.

Converted in this manner into a solid and storable form, the intrinsically viscous 2,2,6,6-tetra(β-carboxyethyl)cyclohexanone tetraglycidyl ester can also later be processed very readily to the actual powder coating composition.

EXAMPLE 3

Preparation of a powder coating composition

A mixture of 420 g of the masterbatch of Example 2, a further 98 g of Crylcoat ® 430, 5.2 g of solid Acrylron ® (flow control agent based on a butylated polyacrylate), 1.2 g of benzoin and 259 g of titanium dioxide is homogenised in an extruder similar to that used in Example 2. The extrudate is milled to the finished powder coating composition having a particle size of c. 40 μm.

This composition is sprayed electrostatically onto an aluminium sheet. After stoving for 20 minutes at a temperature of 200° C. a film having the following properties is obtained:

| | |
|---|---|
| film thickness | 60 μm |
| impact strength | 160 kg · cm |
| Erichsen cupping test (DIN 53 156) | 11.1 mm |
| gloss at an angle of 60° | 100% |
| flow at 200° C. | good |
| yellowness (DIN 6167/ASTM D 1925-70) | 0.5 |

The impact strength is determined by dropping a die of known weight from a specific height onto the back of the coated surface. The value obtained is the product of the weight of the die in kg and the greatest height in cm at which the coating still remains intact. The flow is assessed visually as fair, good or very good.

EXAMPLE 4

In accordance with the procedure described in Example 2, a masterbatch is prepared comprising, in place of Crylcoat ® 430, the same amount of Crylcoat ® 2988 (carboxyl-terminated polyester of neopentanediol and aromatic dicarboxylic acids having an acid value of c. 30 equivalents of KOH/g and a glass transition temperature ($T_G$) of c. 60° C. (DSC), ex UCB, Belgium), and processed to a powder coating composition as in Example 3. After spraying onto aluminium and stoving for 15 minutes at 200° C., a film having the following properties is obtained:

| | |
|---|---|
| film thickness | 55 μm |
| Erichsen cupping test (DIN 53 156) | 6.0 mm |
| gloss at an angle of 60° | 90% |
| flow at 200° C. | good |

The coating has a substantially greater flexibility than the equivalent coating based on triglycidyl isocyanurate as hardener, while having approximately the same weather resistance.

EXAMPLE 5

Preparation and glycidylation of glycerol 1,3-bis(trimellitate)

960.7 g (5 mol) of trimellitic anhydride are dissolved in 4500 ml of methyl isobutyl ketone at 115° C. Then 230.3 g (2.5 mol) of glycerol are added over 40 minutes at 110° C. The reaction mixture is then refluxed for 4 hours. In the course of the reaction, a white suspension of the crude product forms. Filtration gives 464 g of white crude product. This product is purified with 300 ml of methyl isobutyl ketone and dried at 70° C. under a vacuum of c. 0.13 bar. Titration gives 11.0 equivalents/kg of free acid groups (theory: 8.40 equivalents).

To 230 g of the dried product are added 2350 g (25 mol) of epichlorohydrin, while keeping the temperature at 90° C. Then 20 g of a 50% aqueous solution of tetramethylammonium chloride are added, whereupon a readily controllable exothermic reaction ensues. The temperature is kept between 88° and 92° C., and the reaction course is monitored using a pH electrode. After c. 90 minutes the pH meter registers a sudden rise to a value of c. 10.8, thereby indicating the end of the addition reaction. After removal of the pH electrode, the reaction mixture is cooled to 50° C. and another 20 g of the 50% aqueous solution of tetramethylammonium chloride are added. Under a vacuum of 0.09 to 0.13 bar and at a temperature of 45°–50° C., 223.5 g of a 50% aqueous solution of sodium hydroxide are run in continuously while distilling the resulting water from the reaction mixture with epichlorohydrin as an azeotropic mixture. The epichlorohydrin is separated from the water in a water separator and returned to the reaction mixture continuously. A total of c. 170 g of water can be separated. Afterwards the reaction mixture is washed with 200 ml of a 10% aqueous solution of monosodium phosphate and with 3×300 ml of water. The washed reaction mixture is concentrated on a rotary evaporator under a water jet vacuum. The residue is dried for 30 minutes at 125° C./0.0013 bar, giving 270 g (61% of theory) of product in the form of a yellow viscous oil (epoxy value 5.2 equivalents, corresponding to 91% of theory.

EXAMPLE 6

Preparation and glycidylation of the hemiester of hydrogenated bisphenol A and phthalic acid The reaction is carried out substantially as described in Example 5, initially giving 520.9 g of the hemiester as a white solid with an acid value of 3.67 equivalents/kg (99% of theory) from the reaction of 500 g (3.37 mol) of phthalic anhydride and 405.7 g (1.68 mol) of hydrogenated bisphenol A in 2000 g of methyl isobutyl ketone. Then 520 g (1.91 equivalents) of this hemiester are reacted using 3534 g (38.2 mol) of epichlorohydrin, 168 g of a 50% aqueous solution of sodium hydroxide and two times 32 g of a 50% aqueous solution of tetramethylammonium chloride, to give 607.4 g (98% of theory) of the desired solid product with a epoxy value of 2.97 equivalents/kg (96.4% of theory) and a chlorine content of 0.51%.

EXAMPLE 7

Preparation and glycidylation of glycerol 1,3-diphthalate

The reaction is carried out substantially as described in Example 5, initially giving 1165 g (100% of theory) of the desired hemiester as a pale yellow solid with an acid value of 5.27 equivalents/kg from the reaction of 888.7 g (6 mol) of phthalic anhydride and 276.3 g (3 mol) of glycerol in 960 g of methyl isobutyl ketone. Then 450 g (2.37 equivalents) of this hemiester are reacted using 2193 g (23.7 mol) of epichlorohydrin, 208.6 g of a 50% aqueous solution of sodium hydroxide and two times 21 g of a 50% aqueous solution of tetramethylammonium chloride, to give 509.4 g (86% of theory) of the desired yellow viscous product having an epoxy value of 3.38 equivalents/kg (85% of theory) and a chlorine content of 1.4%.

EXAMPLE 8

Preparation and glycidylation of the hemiester of hydrogenated bisphenol A and trimellitic acid The reaction is carried out substantially as described in Example 5, initially giving 507.5 g (100% of theory) of the desired hemiester as a pale yellow solid with an acid value of 6.3 equivalents/kg from the reaction of 300 g (1.56 mol) of trimellitic anhydride and 187.6 g (0.78 mol) of hydrogenated bisphenol A in 3600 g of methyl isobutyl ketone. Then 505 g (3.18 equivalents) of this hemiester are reacted using 5299 g (57.3 mol) of epichlorohydrin, 280 g of a 50% aqueous solution of sodium hydroxide and two times 46 g of a 50% aqueous solution of tetramethylammonium chloride, to give 593.0 g (88% of theory) of the desired yellow viscous tetraglycidyl ester having an epoxy value of 4.32 equivalents/kg (92% of theory) and a chlorine content of 1.94%.

EXAMPLE 9

Preparation and glycidylation of the hemiester of trimethylolpropane and hexahydrophthalic acid 330.1 g (2.14 mol) of hexahydrophthalic anhydride and 93.9 g (0.70 mol) of trimethylolpropane are charged to a reactor and heated, with stirring, to 130° C. After 180 minutes at 130° C., titration of a sample gives 5.30 equivalents/kg of free acid groups (95% of theory). The entire hemiester is reacted further in the same reactor using 1942 g (21 mol) of epichlorohydrin, 185 g of a 50% aqueous solution of sodium hydroxide and two times 19 g of a 50% aqueous solution of tetramethylammonium chloride as in Example 5, to give 529.6 g (98.9% of theory) of the desired yellow, highly viscous triglycidyl ester having an epoxy value of 3.65 equivalents/kg (93.1% of theory) and a chlorine content of 0.86%.

EXAMPLE 10

Preparation and glycidylation of the hemiester of bis(trimethylolpropane) and hexahydrophthalic acid 539.6 g (3.5 mol) of hexahydrophthalic anhydride and 219.0 g (0.87 mol) of bis(trimethylolpropane) are charged to a reactor and heated, with stirring, to 130° C. After 120 minutes at 130° C., titration of a sample gives 5.0 equivalents/kg of free acid groups. The entire hemiester is reacted further in the same reactor using 3228 g (35 mol) of epichlorohydrin, 308 g of a 50% aqueous solution of sodium hydroxide and two times 32 g of a 50% aqueous solution of tetramethylammonium chloride as in Example 5, to give 853.8 g (89% of theory) of the desired pale yellow, highly viscous triglycidyl ester having an epoxy value of 3.75 equivalents/kg (100% of theory) and a chlorine content of 1.20%.

EXAMPLE 11

A mixture of 682 g of Crylcoat ® 430, 114 g of the glycidyl ester of Example 5, 6 g of solid Modaflow ®, 1.2 g of benzoin and 300 g of titanium dioxide is homogenised in an extruder (Ko-kneader supplied by BUSS, Pratteln, CH), preparing first a masterbatch from the viscous glycidyl ester and a sufficient amount of the polyesters as described in Examples 2 and 3. The cooled extrudate is milled to a particle size of c. 40 μm. The powder coating composition so obtained is sprayed electrostatically onto an aluminium sheet and stoved for 20 minutes at a temperature of 200° C. to give a film having the following properties:

| film thickness | 57 μm |
| --- | --- |
| impact strength | 160 kg · cm |
| Erichsen cupping test (DIN 53 156) | 9.9 mm |
| gloss at an angle of 60° | 90% |
| gloss under an angle of 60° after | 65% |
| 450 h weathering in a Weather-O-meter | |
| flow at 200° C. | good |
| yellowness (DIN 6167/ASTM D 1925-70) | 1.2 |

The weathering test is carried out in this Example, as also in the following Examples, in an Atlas ® Weather-O-Meter using the Atlas NBR 180 weathering cycle.

EXAMPLE 12

A powder coating composition comprising 426 g of Crylcoat ® 2988, 75 g of the glycidyl ester of Example 5, 5.5 g of Modaflow ® solid, 1.2 g of benzoin and 266 g of titanium dioxide is homogenised as described in Example 11. The powder coating composition so obtained is sprayed electrostatically onto an aluminium sheet and stoved for 30 minutes at a temperature of 200° C. to give a film having the following properties:

| film thickness | 62 μm |
| --- | --- |
| impact strength | 160 kg · cm |
| Erichsen cupping test (DIN 53 156) | 9.6 mm |
| gloss at an angle of 60° | 90% |
| gloss at an angle of 60° after | 74% |
| 700 h weathering in a Weather-O-meter | |
| flow at 200° C. | good |
| yellowness (DIN 6167/ASTM D 1925-70) | 1.9 |

This powder coating composition gives a coating of substantially greater flexibility than one obtained with a corresponding formulation containing triglycidyl isocyanurate as hardener. The coating has much superior weather resistance to, and the same flexibility as, obtained with a conventional powder coating composition based on e.g. Crylcoat ® 430 as polyester and triglycidyl isocyanurate as hardener.

EXAMPLE 13

A powder coating composition comprising 746 g of Crylcoat ® 430, 190 g of the glycidyl ester of Example 8, 10 g of Modaflow ® solid, 2 g of benzoin and 500 g of titanium dioxide is homogenised as described in Example 11. The powder coating composition so obtained is sprayed electrostatically onto an aluminium sheet and stoved for 30 minutes at a temperature of 200° C. to give a film having the following properties:

| film thickness | 56 μm |
| --- | --- |
| impact strength | 160 kg · cm |
| Erichsen cupping test (DIN 53 156) | 9.9 mm |
| gloss under an angle of 60° | 90% |
| flow at 200° C. | good |
| yellowness (DIN 6167/ASTM D 1925-70) | 0.6 |

EXAMPLE 14

A powder coating composition comprising 597 g of Crylcoat ® 2988, 160 g of the glycidyl ester of Example 8, 8.8 g of solid Modaflow ®, 1.6 g of benzoin and 400 g of titanium dioxide is homogenised as described in Example 11. The powder coating composition so obtained is sprayed electrostatically onto an aluminium sheet and stoved for 30 minutes at a temperature of 200° C. to give a film having the following properties:

| film thickness | 61 μm |
| --- | --- |
| impact strength | 160 kg · cm |
| Erichsen cupping test (DIN 53 156) | 9.8 mm |
| gloss at an angle of 60° | 91% |
| gloss at an angle of 60° after | 73% |
| 700 h weathering in a Weather-O-meter | |
| flow at 200° C. | good |
| yellowness (DIN 6167/ASTM D 1925-70) | 1.4 |

This powder coating composition gives a coating of substantially greater flexibility than one obtained with a corresponding formulation containing triglycidyl isocyanurate as hardener. The coating has much superior weather resistance to, while having the same flexibility as, one obtained with a conventional powder coating composition based on e.g. Crylcoat ® 430 as polyester and triglycidyl isocyanurate as hardener.

EXAMPLE 15

A powder coating composition comprising 630 g of Crylcoat ® 430, 120 g of the glycidyl ester of Example 9, 7.5 g of solid Modaflow ®, 1.5 g of benzoin and 375 g of titanium dioxide is homogenised as described in Example 11. The powder coating composition so obtained is sprayed electrostatically onto an aluminium sheet and stoved for 30 minutes at a temperature of 200° C. to give a film having the following properties:

| | |
|---|---|
| film thickness | 79 μm |
| impact strength | 160 kg · cm |
| Erichsen cupping test (DIN 53 156) | 9.9 mm |
| gloss at an angle of 60° | 92% |
| gloss at an angle of 60° after 450 h weathering in a Weather-O-meter | 80% |
| flow at 200° C. | good |
| yellowness (DIN 6167/ASTM D 1925-70) | 0 |

EXAMPLE 16

A powder coating composition comprising 493 g of Crylcoat ® 430, 107 g of the glycidyl ester of Example 10, 6 g of Acrylron ® MFP (flow control agent based on a butylated polyacrylate which has been stabilised on silicic acid), 1.2 g of benzoin and 300 g of titanium dioxide is homogenised as described in Example 11. The powder coating composition so obtained is sprayed electrostatically onto an aluminium sheet and stoved for 30 minutes at a temperature of 200° C. to give a film having the following properties:

| | |
|---|---|
| film thickness | 66 μm |
| impact strength | 160 kg · cm |
| Erichsen cupping test (DIN 53 156) | 10.1 mm |
| gloss at an angle of 60° | 87% |
| flow at 200° C. | good |
| yellowness (DIN 6167/ASTM D 1925-70) | 0 |

What is claimed is:

1. A powder coating composition comprising at least one polyglycidyl compound and a polyester resin which reacts therewith, wherein the polyglycidyl compound is a polyglycidyl ester of formula (II)

$$R_7\text{---}[Z]_n, \quad (II)$$

wherein in formula (II)
n is an integer from 2 to 6,
$R_7$ is an organic radical of valency n of 2 to 30 carbon atoms, and
Z denotes identical or different radicals of formula (IV)

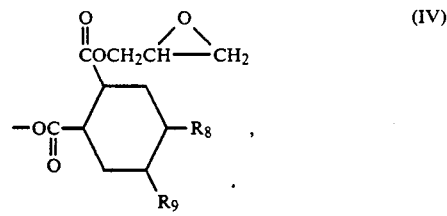

wherein $R_8$ and $R_9$ are either each independently of the other hydrogen, chloro, bromo or $C_1$-$C_4$alkyl or one is a radical of formula (V)

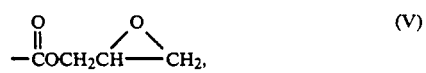

and the other is hydrogen, chloro, bromo or $C_1$-$C_4$alkyl, and the six-membered ring in formula (IV) is aromatic or non-aromatic.

2. A powder coating composition according to claim 1, wherein the polyester carries terminal carboxyl groups.

3. A powder coating composition according to claim 2 which comprises a polyglycidyl ester of formula (II), wherein $R_7$ is a divalent to tetravalent radical which is derived from an aliphatic polyalcohol or polyether alcohol of 2 to 10 carbon atoms by removal of two to four hydroxyl groups, or $R_7$ is a divalent to tetravalent radical of the molecular formula

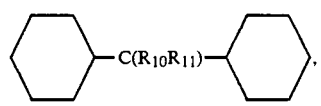

wherein $R_{10}$ and $R_{11}$ are each independently of the other hydrogen or methyl and the six-membered carbon rings may be aromatic or non-aromatic.

4. A powder coating composition according to claim 1, wherein the polyester has a content of up to 90 percent and more of neopentanediol and aromatic dicarboxylic acids as components.

5. A powder coating composition according to claim 2, which comprises a polyglycidyl ester of formula (II) which contains four glycidyl groups.

* * * * *